(12) United States Patent
Anraku et al.

(10) Patent No.: US 7,726,498 B2
(45) Date of Patent: Jun. 1, 2010

(54) HERMETICALLY SEALED CONTAINER AND VACUUM TEST SUBSTANCE-COLLECTING CONTAINER

(75) Inventors: Hideo Anraku, Shunan (JP); Masahiro Nakaizumi, Shunan (JP); Mitsuru Naruta, Shunan (JP)

(73) Assignee: Sekisui Chemical Co., Ltd., Osaka (JP)

( * ) Notice: Subject to any disclaimer, the term of this patent is extended or adjusted under 35 U.S.C. 154(b) by 308 days.

(21) Appl. No.: 10/564,718
(22) PCT Filed: Jul. 16, 2004
(86) PCT No.: PCT/JP2004/010204
§ 371 (c)(1),
(2), (4) Date: Mar. 23, 2006
(87) PCT Pub. No.: WO2005/011495
PCT Pub. Date: Feb. 10, 2005

(65) Prior Publication Data
US 2006/0175280 A1 Aug. 10, 2006

(30) Foreign Application Priority Data
Jul. 18, 2003 (JP) .............................. 2003-276989

(51) Int. Cl.
*B65D 39/00* (2006.01)
(52) U.S. Cl. .................. 215/247; 215/354; 215/355; 215/364; 604/415
(58) Field of Classification Search ............... 215/247, 215/271, 320, 354, 355; 220/231, 801, 802, 220/DIG. 19; 600/573; 604/415
See application file for complete search history.

(56) References Cited

U.S. PATENT DOCUMENTS 3,499,568 A * 3/1970 Vinas Riera ................. 215/276

(Continued)

FOREIGN PATENT DOCUMENTS

EP 1064879 A1 * 1/2001

(Continued)

OTHER PUBLICATIONS eFunda Polymers: Properties of Polyethylene and Ethylene Copolymers—HDPE. www.efunda.com.*

(Continued)

*Primary Examiner*—Anthony Stashick
*Assistant Examiner*—Ned A Walker
(74) *Attorney, Agent, or Firm*—Sughrue Mion, PLLC

(57) ABSTRACT

It is the object of the present invention to provide a sealed container which comprises a container comprising a thermoplastic resin and a stopper which is hardly slackening even when used in combination with the container, and a vacuum specimen-sampling container comprising the sealed container.

The present invention is a sealed container, which comprises a container with an end being closed and the other end being open, comprising a thermoplastic resin, and a stopper being detachable and capable of sealing the open end of the container, the stopper having a head portion capable of being grasped, a leg portion A being extended downward from the head portion, being along an internal wall surface of the open end of the container, and being capable of exerting a fitting force to the internal wall surface, and a leg portion B being extended downward from the head portion, being along an external wall surface of the open end of the container, and being capable of exerting a fitting force to the external wall surface, and at least a portion of the leg portion B of the stopper contacting with the container and at least a portion of the container contacting with the leg portion A of the stopper having a deflection temperature under load of 60° C. or more under a load of 0.45 MPa or 0.46 MPa.

13 Claims, 11 Drawing Sheets

U.S. PATENT DOCUMENTS

| | | | | |
|---|---|---|---|---|
| 4,019,646 A * | 4/1977 | Imamura | | 215/329 |
| 4,094,429 A * | 6/1978 | Urbin | | 215/305 |
| 4,416,661 A * | 11/1983 | Norman et al. | | 604/86 |
| 4,465,200 A * | 8/1984 | Percarpio | | 215/247 |
| 4,569,457 A * | 2/1986 | Hatakeyama et al. | | 215/364 |
| 4,664,274 A * | 5/1987 | Konrad | | 215/232 |
| 4,697,717 A * | 10/1987 | Grippi | | 215/354 |
| 4,747,839 A * | 5/1988 | Tarello et al. | | 604/240 |
| 4,813,578 A * | 3/1989 | Gordon et al. | | 222/541.1 |
| 4,967,919 A * | 11/1990 | Earhart | | 215/247 |
| 5,033,476 A | 7/1991 | Kasai | | |
| 5,100,010 A * | 3/1992 | Waters | | 215/248 |
| 5,219,083 A * | 6/1993 | Liebert et al. | | 215/247 |
| 5,275,299 A * | 1/1994 | Konrad et al. | | 215/341 |
| 5,306,270 A * | 4/1994 | Macartney et al. | | 604/415 |
| 5,361,921 A * | 11/1994 | Burns | | 215/320 |
| 5,370,252 A * | 12/1994 | Parsons et al. | | 215/247 |
| 5,433,330 A * | 7/1995 | Yatsko et al. | | 215/247 |
| 5,494,170 A | 2/1996 | Burns | | |
| 5,522,518 A * | 6/1996 | Konrad et al. | | 215/247 |
| 5,738,233 A * | 4/1998 | Burns | | 215/247 |
| 5,819,964 A * | 10/1998 | Grimard | | 215/249 |
| 5,819,978 A * | 10/1998 | Hlebovy | | 220/601 |
| 5,823,373 A * | 10/1998 | Sudo et al. | | 215/249 |
| 5,857,580 A * | 1/1999 | Iidaka | | 215/256 |
| 6,003,566 A * | 12/1999 | Thibault et al. | | 141/25 |
| 6,189,580 B1 * | 2/2001 | Thibault et al. | | 141/25 |
| 6,213,994 B1 * | 4/2001 | Jansen et al. | | 604/415 |
| 6,378,576 B2 * | 4/2002 | Thibault et al. | | 141/329 |
| 6,378,714 B1 * | 4/2002 | Jansen et al. | | 215/249 |
| 6,382,442 B1 * | 5/2002 | Thibault et al. | | 215/249 |
| 6,565,814 B1 | 5/2003 | Anraku et al. | | |
| 6,602,206 B1 * | 8/2003 | Niermann et al. | | 600/573 |
| 6,626,309 B1 * | 9/2003 | Jansen et al. | | 215/249 |
| 6,681,946 B1 * | 1/2004 | Jansen et al. | | 215/249 |
| 6,716,396 B1 * | 4/2004 | Anderson et al. | | 422/99 |
| 6,723,289 B2 * | 4/2004 | Iheme et al. | | 422/100 |
| 6,806,094 B2 * | 10/2004 | Anderson et al. | | 436/180 |
| 6,821,267 B2 * | 11/2004 | Veillon et al. | | 604/192 |
| 6,945,417 B2 * | 9/2005 | Jansen et al. | | 215/249 |
| 7,097,057 B2 * | 8/2006 | Claessens | | 215/247 |
| 2001/0039058 A1 * | 11/2001 | Iheme et al. | | 436/180 |
| 2001/0041336 A1 * | 11/2001 | Anderson et al. | | 435/6 |
| 2003/0029828 A1 * | 2/2003 | Amschlinger et al. | | 215/247 |
| 2003/0171719 A1 * | 9/2003 | Veillon et al. | | 604/187 |
| 2003/0207463 A1 * | 11/2003 | Iheme et al. | | 436/180 |
| 2004/0099629 A1 * | 5/2004 | Whitley | | 215/276 |
| 2004/0118803 A1 | 6/2004 | Claessens | | |
| 2004/0256348 A1 * | 12/2004 | Stevens et al. | | 215/262 |
| 2005/0010175 A1 * | 1/2005 | Beedon et al. | | 604/218 |

FOREIGN PATENT DOCUMENTS

| | | |
|---|---|---|
| JP | SHO-52-112481 | 9/1977 |
| JP | SHO-57-059536 | 4/1982 |
| JP | SHO-58-142256 | 8/1983 |
| JP | SHO-62-227316 | 10/1987 |
| JP | HEI-03-505320 | 10/1989 |
| JP | HEI-03-097450 | 4/1991 |
| JP | HEI-04-279152 | 10/1992 |
| JP | HEI-07-051253 | 2/1995 |
| JP | 2608682 A | 2/1997 |
| JP | HEI-10-201742 | 8/1998 |
| JP | 11-318868 A | 11/1999 |
| JP | HEI-11-318868 | 11/1999 |
| JP | 2001-149350 | 6/2001 |
| JP | 2001-149350 A | 6/2001 |
| JP | 2002-068230 A | 3/2002 |
| WO | 01/47636 A2 | 7/2001 |

OTHER PUBLICATIONS

MatWeb—Division of Automation Creation, Inc. Plastic Material Data Sheets, 2004. Table: Typical Properties of Polyurethane Thermoplastic Elastomer.*

Matweb by Automation Creations, Inc. "Deflection Temperature Testing of Plastics—Typical Deflection Temperatures and Melting Points of Polymers", Archive dated Jun. 5, 2002, retrieved Feb. 10, 2009 using Archive.org.*

"Deflection Temperature Testing of Plastics" [Online} XP002547243 Retrieved from the Internet: URL:http://www.matweb.com/reference/deflection-temperature.aspx> [retrieved on Sep. 24, 2009].

EP Office Action dated Dec. 18, 2009; Application No. 04 747 670.0 - 1526.

* cited by examiner

[Fig. 1]
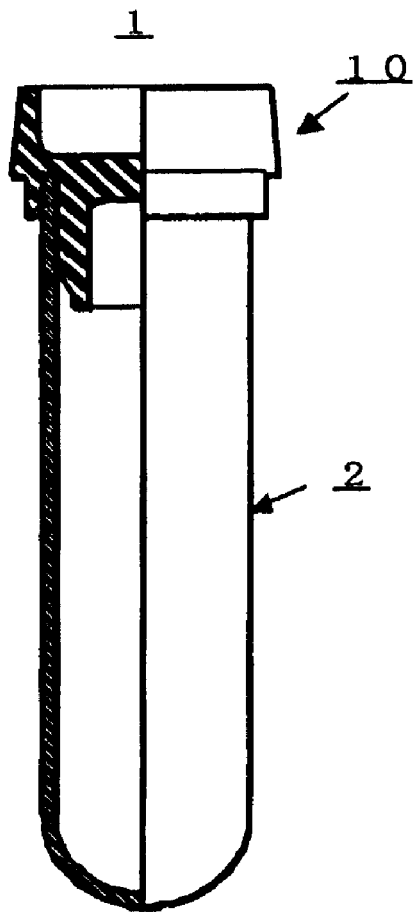
[Fig. 2]
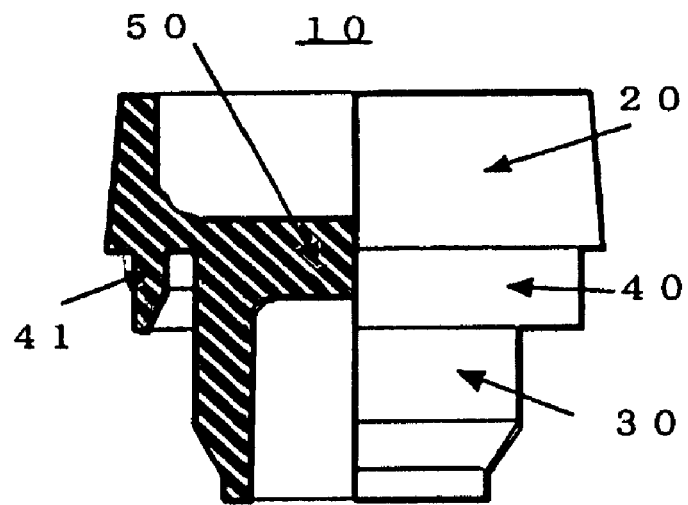

[Fig. 3]
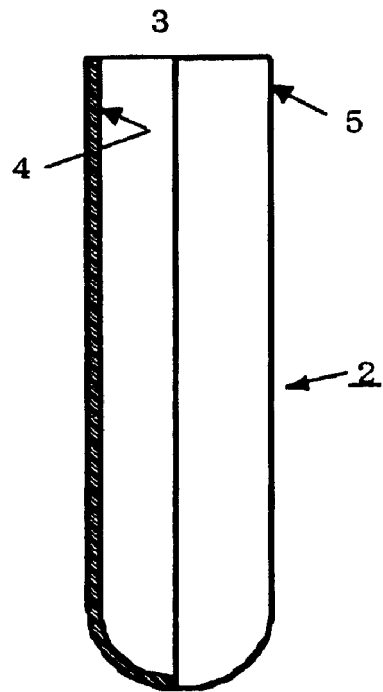
[Fig. 4]
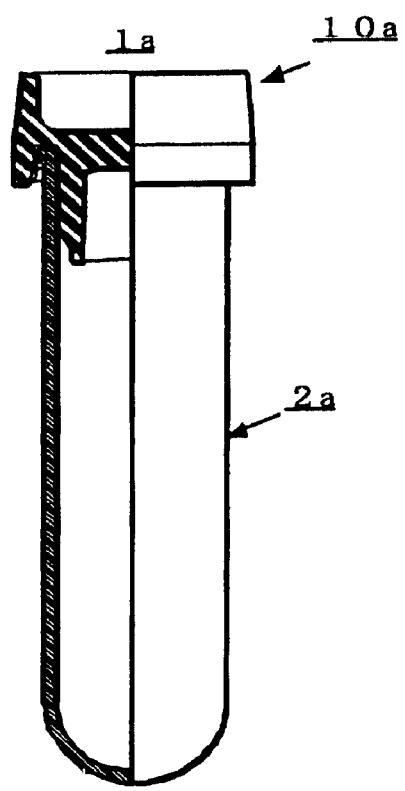

[Fig. 5]
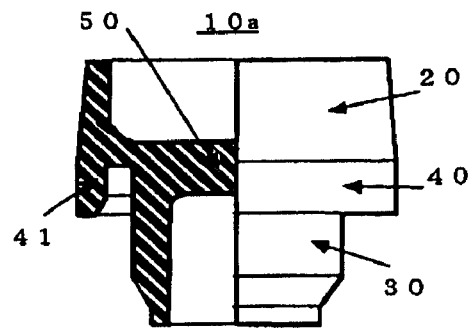
[Fig. 6]
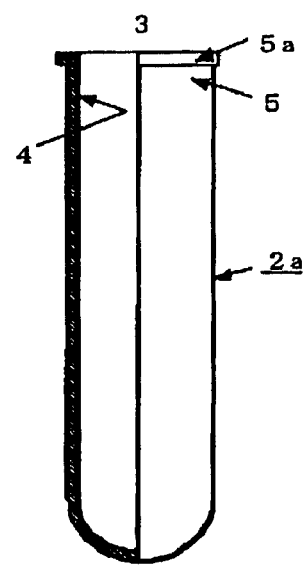
[Fig. 7]
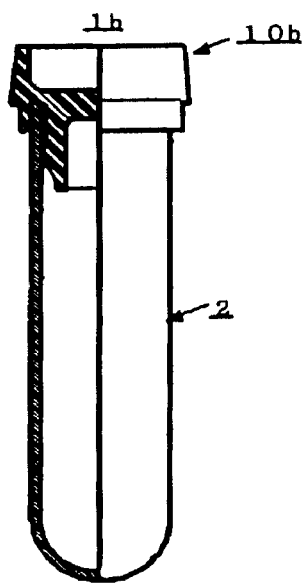

[Fig. 8]
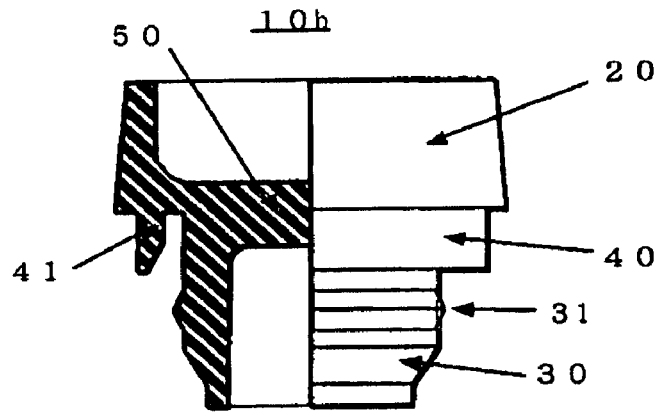
[Fig. 9]
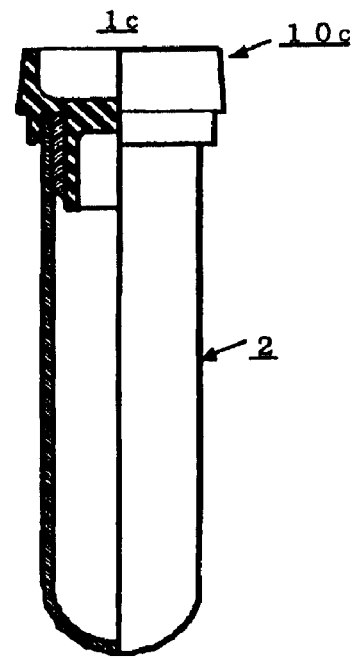
[Fig. 10]
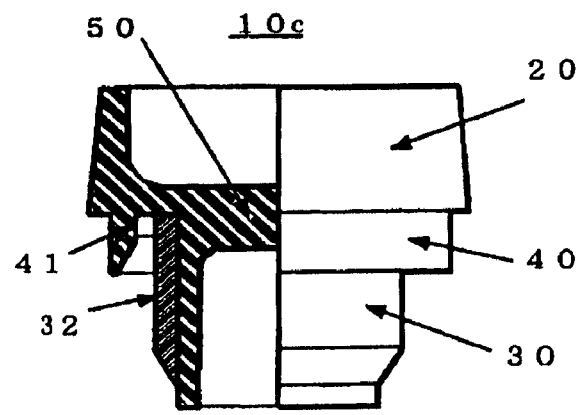

[Fig. 11]
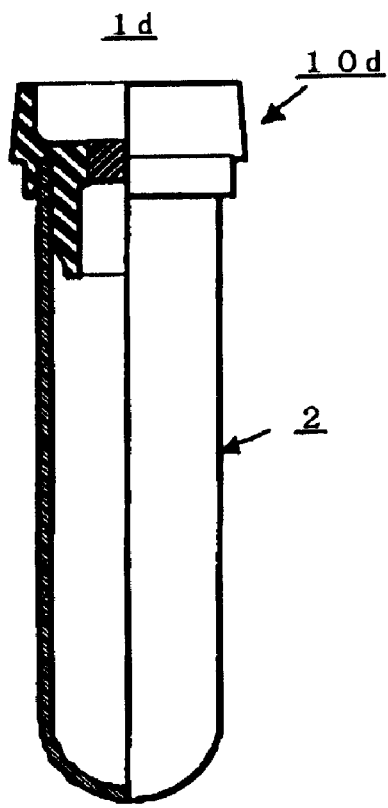
[Fig. 12]
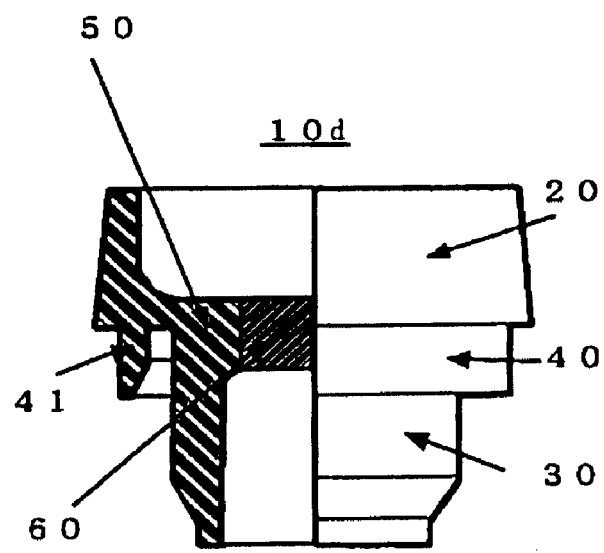

[Fig. 13]
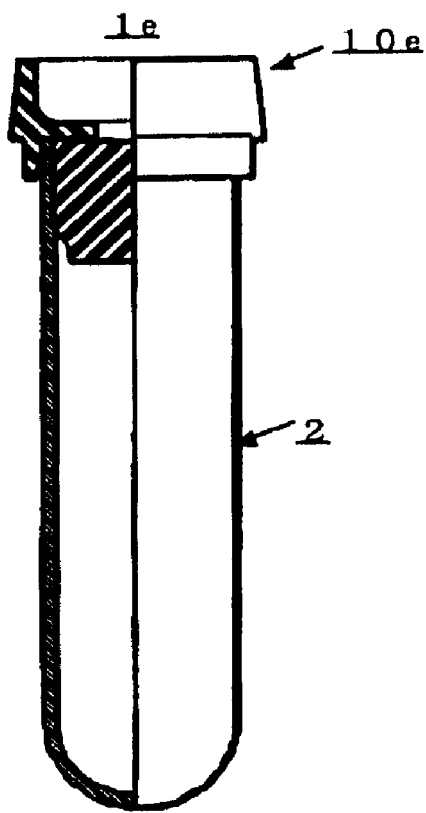
[Fig. 14]
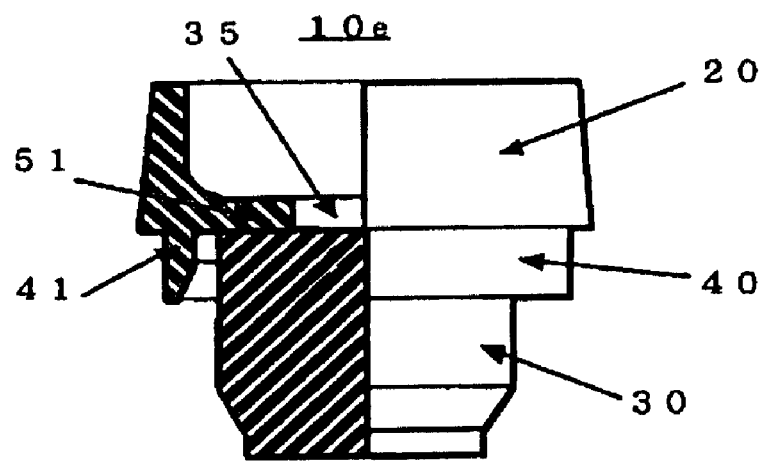

[Fig. 15]
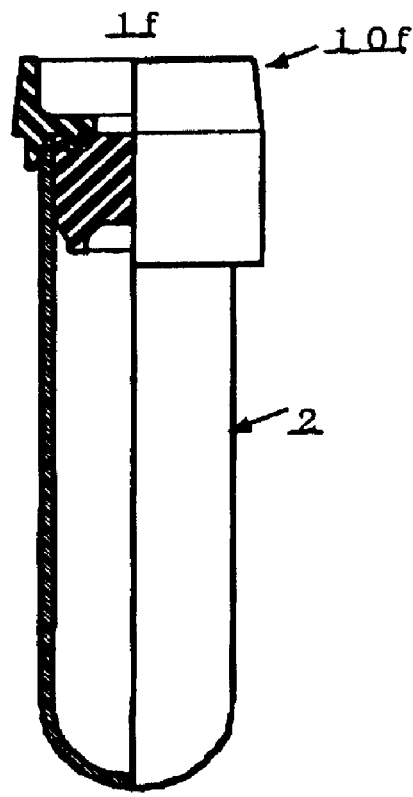
[Fig. 16]
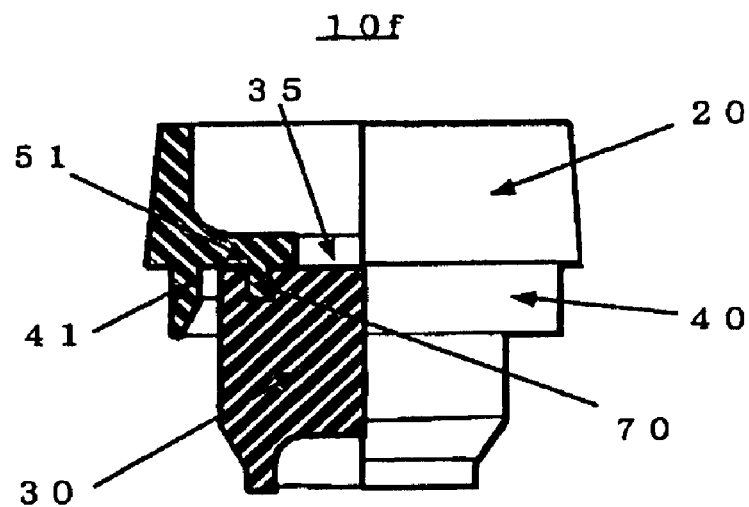

[Fig. 17]
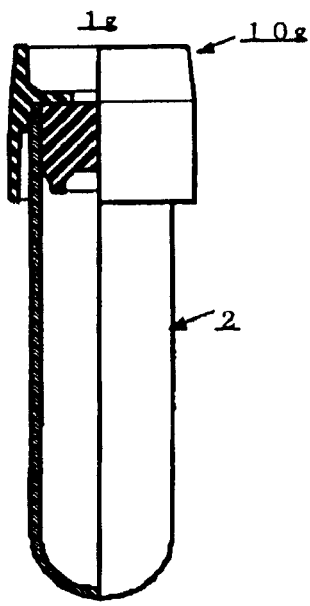
[Fig. 18]
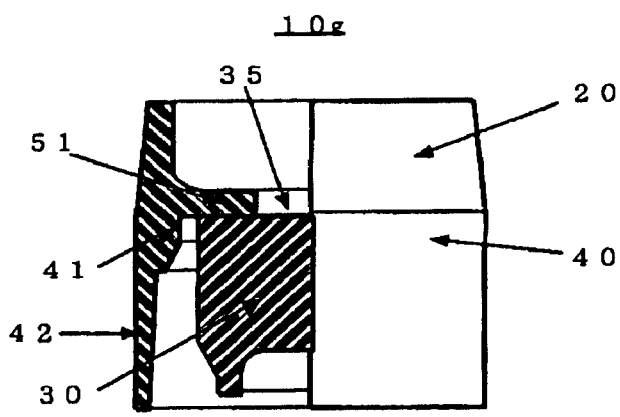
[Fig. 19]
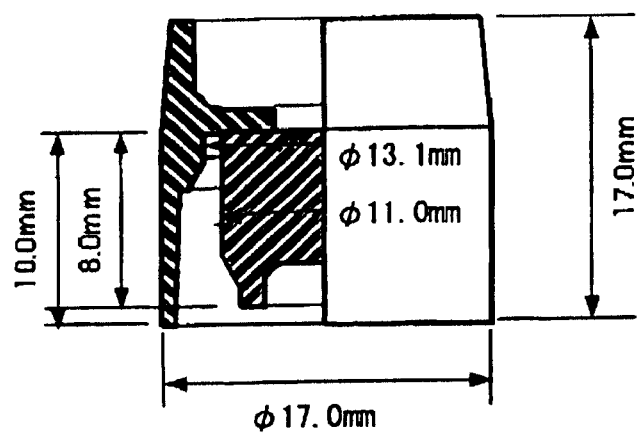

[Fig. 20]
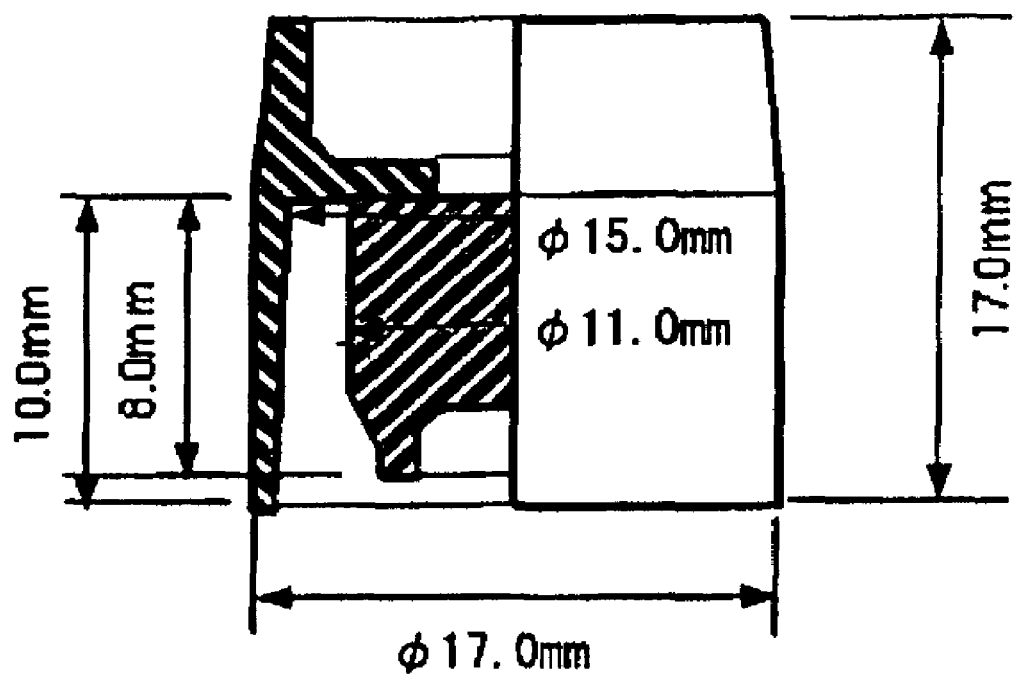

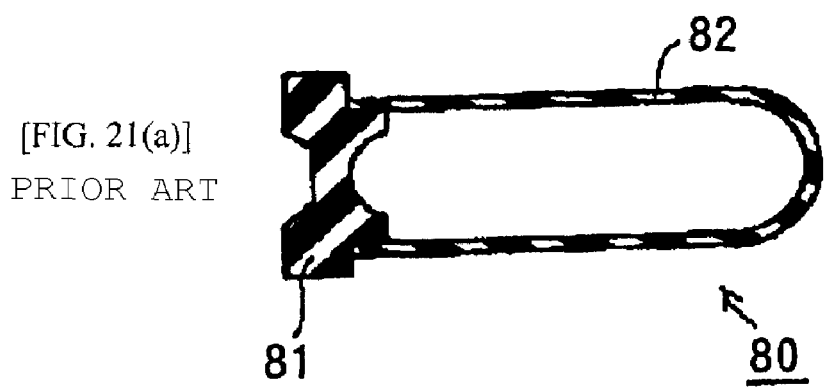
[FIG. 21(a)]
PRIOR ART
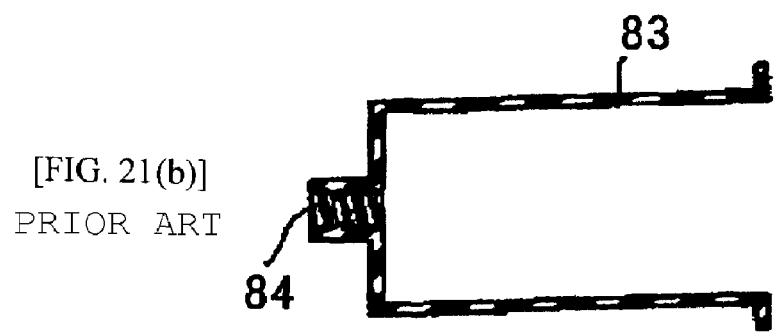
[FIG. 21(b)]
PRIOR ART
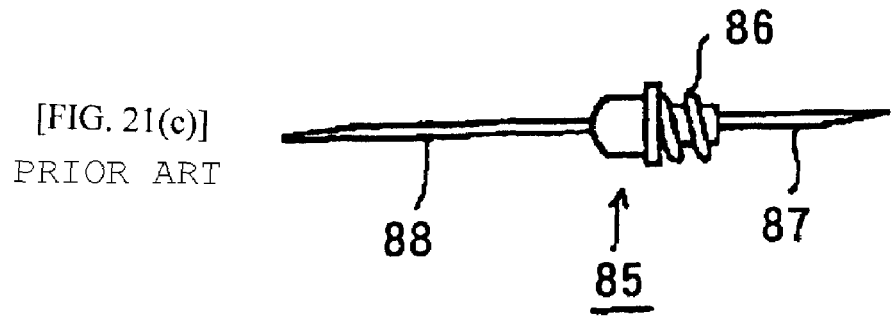
[FIG. 21(c)]
PRIOR ART

[Fig. 22]
PRIOR ART
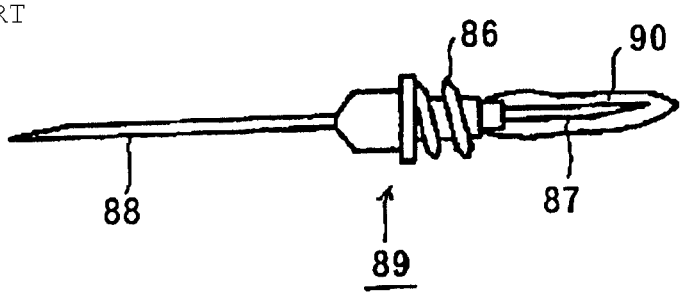
[Fig. 23]
PRIOR ART
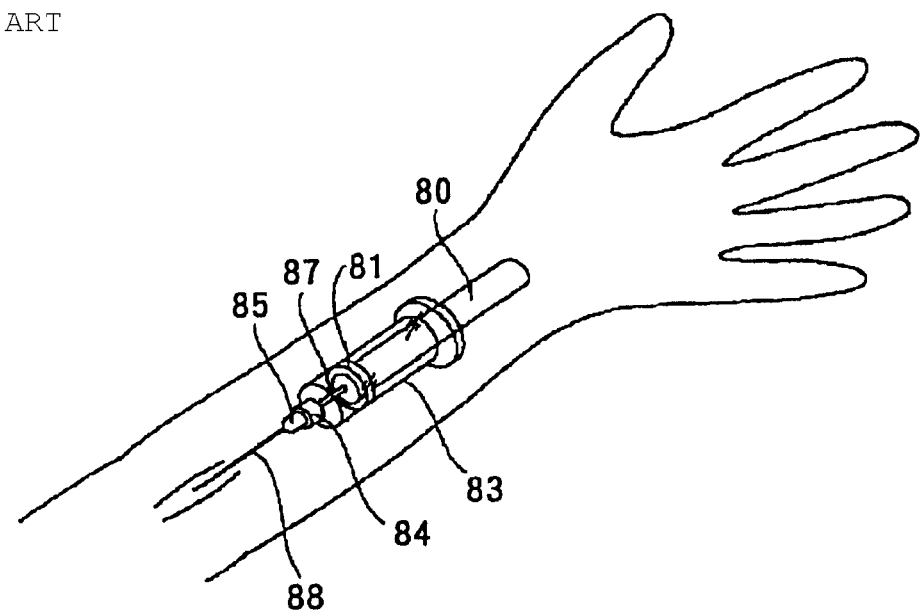
[Fig. 24]
PRIOR ART
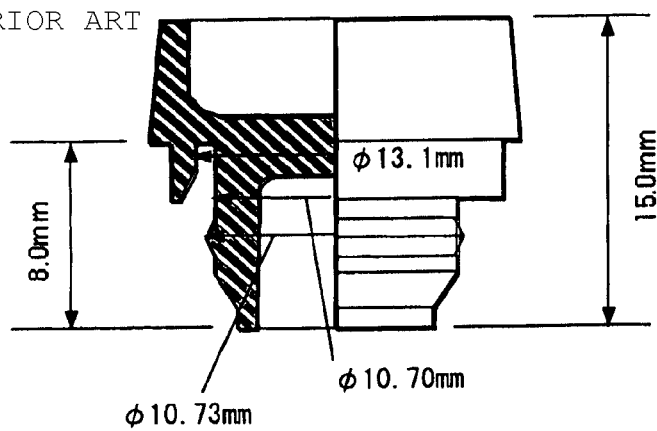

HERMETICALLY SEALED CONTAINER AND VACUUM TEST SUBSTANCE-COLLECTING CONTAINER

TECHNICAL FIELD

The present invention relates to a sealed container which comprises a container comprising a thermoplastic resin and a stopper which is hardly slackening even when used in combination with the container, and a vacuum specimen-sampling container comprising the sealed container.

BACKGROUND ART

Various vacuum specimen-sampling containers, wherein sealed containers, the inside being under a reduced atmospheric pressure state, is known. Among such vacuum specimen-sampling containers, for example, vacuum blood-sampling tubes are most generally used. An example of such vacuum blood-sampling tubes is disclosed in Patent Document 1, for instance.

One example of the vacuum blood-sampling system disclosed in Patent Document 1 is shown in FIGS. 21(a) to 21(c). This vacuum blood-sampling system comprises a vacuum blood-sampling container 80 shown in FIG. 21(a), a vacuum blood-sampling holder 83 shown in FIG. 21(b) and a vacuum blood-sampling needle 85 shown in FIG. 21(c). The vacuum blood-sampling container 80 comprises a blood-sampling tube 82 with an opening at an end and a stopper 81 which seals the opening of the blood-sampling tube 82. The stopper 81 is made of an elastic material having a needle-hole sealing property and a gas barrier property. Here, the vacuum blood-sampling holder 83 is designed so that the vacuum blood-sampling container 80 is inserted therein from the opening at an end. A blood-sampling needle holding hole 84 is formed at the other end of the vacuum blood-sampling holder 83, an internal thread is formed in the blood-sampling needle holding hole 84. On the other hand, the vacuum blood-sampling needle 85 has needle tips 87 and 88 at the both ends. A hub 86 on which an external thread portion is formed is formed on the needle tip 87 side. The hub 86 is designed to be screwed into the blood-sampling needle holding hole 84 of the vacuum blood-sampling holder 83 to be secured therein.

FIG. 23 is a schematic perspective view to explain a method of sampling blood by using the vacuum blood-sampling system disclosed in Patent Document 1. Referring to FIGS. 21(a) to (c) and FIG. 23, the blood-sampling step is explained.

In sampling blood, the vacuum blood-sampling needle 85 is threadedly engaged with the blood-sampling needle holding hole 84 of the vacuum blood-sampling holder 83. Next, the vacuum blood-sampling container 80 is inserted into the holder 83, and pushed in such a degree that the needle tip 87 of the vacuum blood-sampling needle 85 does not penetrate the stopper 81, and the needle tip 87 is once sealed. This makes it possible to prevent blood leaking from the needle tip 87, in insertion of the needle tip 88 into a blood vessel. As shown in FIG. 23, while holding the entire structure of the blood-sampling needle 85, the holder 83 and the blood-sampling container 80 coupled to one after another with the hands in a manner so as to align it along the direction of a blood vessel axis, the blood-sampling operator inserts the tip of the needle 88 on the blood-vessel piercing side into a blood vessel. Next, when the blood-sampling container 80 is further pushed into the holder 83, the needle tip 87 penetrates the stopper 81, and blood flows into the blood-sampling container 80 in accordance with a pressure difference between the blood-sampling container side and the blood vessel side. When the pressure difference between the both sides is reduced to zero, the flow of the blood is stopped, and in this state, the entire blood-sampling system is shifted so that the needle tip 88 is drawn from the blood vessel.

The blood-sampling needle 85 is called as a so-called single blood-sampling needle, which is used when the blood sampling is carried out into a single vacuum blood-sampling container. In carrying out the blood sampling into a plurality of blood-sampling containers, this single blood-sampling needle cannot be used. In other words, since, in exchanging blood-sampling containers, the needle tip 88 needs to be kept inserted into the blood vessel, blood is leaked from the needle tip 87 in the case of using the single blood-sampling needle. In contrast, in the case when a multiple blood-sampling needle 89 having a structure shown in FIG. 22 is used, since an elastic sheath 90 is externally inserted to the needle tip 87 on the stopper piercing side, with the needle tip 87 being coated in an air-tight manner, the leak of blood can be prevented.

In the case when such a multiple blood-sampling needle 89 is used, after an assembled body comprising the multiple blood-sampling needle 89 and the holder 83 is prepared, the needle tip 88 of the multiple blood-sampling needle 89 is inserted into a blood vessel. Then, the blood-sampling container 80 is inserted into the holder 83 so that the blood-sampling container 80 is allowed to communicate with the blood vessel.

With respect to a material used for the blood-sampling tube 82 shown in FIG. 21(a), conventionally, glass has been used, however, in recent years, in place of the blood-sampling tube made of glass, a plastic blood-sampling tube made of a thermoplastic resin having a superior gas-barrier property, such as polyethylene terephthalate, has been used in many cases.

With respect to the elastic material used for the stopper 81 shown in FIG. 21(a), since a superior gas-barrier property is required so as to maintain a proper reduced atmospheric pressure degree inside the blood-sampling container, and since a proper needle-hole sealing property after the withdrawal of the needle tip is required, cross-linking isobutylene-isoprene rubber (cross-linking IIR, cross-linking butyl rubber) has been conventionally used. However, the cross-linking rubber requires a long period of time for a curing reaction step and post-steps, such as water-washing and removing steps of a curing reaction agent and elusive substances derived from side products, etc. of the curing reaction, resulting in degradation in the productivity. For this reason, in recent years, stoppers, prepared by using a thermoplastic resin and a thermoplastic elastomer which can be injection-molded, is proposed, for example, in Patent Documents 2 to 7.

After the blood-sampling by using the vacuum blood-sampling system shown in FIGS. 21(a) to (c), in the case when, for example, a biochemical inspection is carried out thereon, carrying out a centrifugal separation after the completion of coagulation of the blood, serum is obtained as a supernatant fluid so that after the stopper 81 is removed, one portion of the serum is taken by using a pipette and the like and various components, such as electrolytes, enzymes and lipids, are subjected to concentration analyses by using an analyzing device. With respect to the residual specimen, the blood-sampling container is again sealed with the stopper 81 for re-inspection, and stored in a cold state or in a frozen state. In this case, however, when, after a blood-sampling container is once opened and a specimen is partially taken for inspections, the container is re-sealed, the inner air of the container is compressed due to the superior sealing property of the stopper to cause an increase in the inner pressure, and the stopper is gradually raised to eventually come off to often cause a problem, that is, a so-called pop-up phenomenon.

Patent Document 8, on the other hand, discloses a stopper for a bottle having a fit-in structure in which a ring-shaped rib, which protrudes on an internal wall surface or on an external wall surface in the vicinity of an open end of a blood-sampling tube made of glass or plastics, is formed and a ring-shaped groove which is engaged with the ring-shaped rib is formed in a rubber stopper. Moreover, Patent Document 10 discloses an opening and closing device for a cylinder-shaped case in which a screw cap and a rubber stopper are combined with each other.

These fit-in structure or screw cap structure provide effective means for preventing the pop-up phenomenon. However, although the blood-sampling tube made of glass may adopt these structures, the blood-sampling tube made of plastics has a difficulty in adopting these structures because the dimension of the protrusion of the ring-shaped rib to be prepared is limited to only a small one which does not impair the releasing property from the metal mold, unless a complex sliding mechanism is incorporated into a molding metal mold, and it becomes difficult to obtain a clear fitting-in effect. Moreover, the screw cap structure requires frequent attaching and detaching operations to consume much labor in repeating the opening and closing operations of a number of blood-sampling tubes. Since polyethylene terephthalate, which has been adopted as a material for blood-sampling tubes made of plastics in recent years, has a comparatively low thermally deforming temperature of about 65° C., the internal diameter of the blood-sampling tube open portion tends to become larger due to a fitting force exerted by the stopper with a lapse of time, easily resulting in the pop-up phenomenon.

In the case when a thermoplastic resin or a thermoplastic elastomer is used as the stopper, the thermoplastic resin and the thermoplastic elastomer are extremely greater in compression permanent strain in comparison with thermosetting elastomers. For this reason, as time elapses after such a stopper was attached to a blood-sampling tube, in particular, when left for a long time under high temperatures in summer, the fitting force between the stopper and the blood-sampling tube is almost lost in a very short time of days. Therefore, in the case when a stopper made of a thermoplastic resin or a thermoplastic elastomer is used in combination with a blood-sampling tube made of polyethylene terephthalate, a problem arises in which the deformation of the blood-sampling tube and the slackening of the stopper due to the compression permanent strain jointly cause further slackening.

Patent Document 1: Japanese Kokai Publication Sho-62-227316
Patent Document 2: Japanese Kokai Publication Sho-57-59536
Patent Document 3: Japanese Kokai Publication Hei-3-97450
Patent Document 4: Japanese Kokai Publication Hei-4-279152
Patent Document 5: Japanese Kokai Publication Hei-7-51253
Patent Document 6: Japanese Kokai Publication Hei-10-201742
Patent Document 7: Japanese Kokai Publication Hei-11-318868
Patent Document 8: Japanese Kokai Publication Sho-58-142256
Patent Document 9: Japanese Kokai Publication Sho-52-112481
Patent Document 10: Japanese Kohyo Publication Hei-3-505320

DISCLOSURE OF THE INVENTION

Problems Which the Invention is to Solve

In order to solve the above-mentioned problems, it is an object of the present invention to provide a sealed container which comprises a container comprising a thermoplastic resin and a stopper which is hardly slackening even when used in combination with the container, and a vacuum specimen-sampling container comprising the sealed container.

Means for Solving the Object

The first aspect of the present invention is a sealed container, which comprises a container with an end being closed and the other end being open, comprising a thermoplastic resin, and a stopper being detachable and capable of sealing the open end of the container, the stopper having a head portion capable of being grasped, a leg portion A being extended downward from the head portion, being along an internal wall surface of the open end of the container, and being capable of exerting a fitting force to the internal wall surface, and a leg portion B being extended downward from the head portion, being along an external wall surface of the open end of the container, and being capable of exerting a fitting force to the external wall surface, and at least a portion of the leg portion B of the stopper contacting with the container and at least a portion of the container contacting with the leg portion A of the stopper having a deflection temperature under load of 60° C. or more under a load of 0.45 MPa or 0.46 MPa.

The second aspect of the present invention is a sealed container, which comprises a container with an end being closed and the other end being open, comprising a thermoplastic resin, and a stopper being detachable and capable of sealing the open end of the container, the stopper having a head portion capable of being grasped, a leg portion A being extended downward from the head portion, being along an internal wall surface of the open end of the container, and being capable of exerting a fitting force to the internal wall surface, and a leg portion B being extended downward from the head portion, being along an external wall surface of the open end of the container, and being capable of exerting a fitting force to the external wall surface, and a deflection temperature under load of at least a portion of the leg portion B of the stopper contacting with the container under a load of 0.45 MPa or 0.46 MPa is higher than a deflection temperature under load of at least a portion of the container contacting with the leg portion A of the stopper under a load of 0.45 MPa or 0.46 MPa.

The present invention will be described below in detail.

The present invention will be described by means of embodiments shown in figures, however, the present invention is not intended to be limited only by these embodiments.

FIG. 1 is a semi-sectional view which shows a partially cut-out portion of a sealed container in accordance with one embodiment of the present invention. In the sealed container 1 shown in FIG. 1, a stopper 10 is fitted to a container 2. FIG. 2 is a semi-sectional view which shows a partially cut-out portion of the stopper 10, and FIG. 3 is a semi-sectional view which shows a partially cut-out portion of the container 2.

In the container 2, an end is closed and the other end (an open end 3) is open.

The stopper 10 has a head portion 20 capable of being grasped, a partition wall portion 50 which crosses the open end 3 of the container 2, a leg portion A30 which is extended downward from the head portion 20, and is along the internal wall surface 4 of the open end 3 of the container 2, and being capable of exerting a fitting force to the internal wall surface 4, and a leg portion B40 which is extended downward from the head portion 20, and is along the external wall surface 5 of the open end 3 of the container 2, and being capable of exerting a fitting force to the external wall surface 5 in the vicinity 41 of the open end.

In the present description, being capable of exerting a fitting force means that attaching and detaching of the stopper are carried out against a sliding resistance.

In the sealed container 1 having such a structure, when the stopper 10 is fitted to the container 2, the external diameter of the leg portion A30 of the stopper 10 receives a narrowing force, and the internal diameter of the container 2 is subjected to an expanding force. On the other hand, when the internal diameter of the container 2 is expanding, an increased fitting force by the leg portion B40 of the stopper 10 is applied to the container 2.

In the first aspect of the present invention, at least a portion of the leg portion B40 of the stopper 10 contacting with the container 2 and at least a portion of the container 2 contacting with the leg portion A30 of the stopper 10 have a deflection temperature under load of 60° C. or more under a load of 0.45 MPa or 0.46 MPa. In the case when the deflection temperature under load at these portions is less than 60° C., the creep speed of the material of the stopper 10 becomes very high when the sealed container 1 is stored for a long period of time under high temperatures in summer, the fitting force to the container 2 is reduced and lost in a short period of time, and the stopper is easily slackened. It is more preferably 70° C. or more.

In the second aspect of the present invention, a deflection temperature under load at least at a portion of the leg portion B40 of contacting with the container 2 under a load of 0.45 MPa or 0.46 MPa is higher than a deflection temperature under load at least at a portion of the container 2 contacting with the leg portion A30 of the stopper 10 under a load of 0.45 MPa or 0.46 MPa. By properly selecting the combination of the material forming the stopper 10 and the material forming the container 2 so that the degree of deformation under load at least at the portion of the leg portion B40 of the stopper 10 contacting with the external wall surface 5 of the container 2 is not over a degree of deformation under load at the portion of the container 2 contacting with the leg portion A30, the internal diameter of the open end of the container 2 is prevented from being expanded due to a fitting force exerted from the outside of the container 2 by the leg portion B40 of the stopper, thereby making it possible to prevent the stopper 10 from coming off due to slackening.

The degree of deformation under load can be evaluated by any one of the deflection temperature under load, the vicut softening point and the tensile creep extension.

The deflection temperature under load (also referred to as thermal deformation temperature) is measured by a method in accordance with, for example, ISO75, ISO1873, ASTM D648, JIS K 6921, JIS K 7191 and the like.

The vicut softening point is measured by a method in accordance with, for example, ISO 306, ASTM D648, ASTM D1525, JIS K 7206 and the like.

The tensile creep extension is measured by a method in accordance with JIS K 7115 and the like.

In evaluation by using the deflection temperature under load or the vicut softening point as an index, as the temperature at which a fixed amount of deformation or a fixed amount of intrusion has been reached under a fixed load becomes lower, it is determined that the heat resistance is lower. In evaluation by using the tensile creep extension as the index, as the change in the length of a test piece under fixed temperature, load and load-applying time becomes greater, it is determined that the heat resistance is lower.

Of these, the test method which best reflects the slackening phenomenon in fitting of the stopper is the tensile creep extension method, however, in the present invention, it is determined by the deflection temperature under load, since the measurement is easily carried out.

In measuring the deflection temperature under load and the like based on the standards, not a product shape such as an actual stopper, but a test piece having a predetermined shape, needs to be used, however, since the crystallinity of the test piece gives effects to measured values, a test piece of which the crystallinity is close to that of an actual stopper molded product need to be used.

In a sealed container 1 which is one example of an embodiment in accordance with the second aspect of the present invention, the distance of the leg portion B40 of the stopper 10 contacting with the external wall surface 5 of the container 2 is preferably shorter than the distance of the leg portion A30 contacting with the internal wall surface 4 of the container 2 in the longitudinal direction of the container 2. When the distance of the leg portion B40 of the stopper 10 contacting with the external wall surface of the container 2 is shorter than the distance of the leg portion A30 contacting with the internal wall surface of the container 2 in the longitudinal direction of the container main body 2, the container internal diameter at a portion on the bottom side from the open end which is not subjected to a fitting force of the leg portion B40 causes a creeping due to a fitting force exerted from the inside of the leg portion A30, thereby it is expanding. Consequently, the container is deformed into a shape with a narrowed opening so that the coming off of the stopper 10 due to slackening is prevented more effectively. Therefore, even when the sealed container 1 is laterally laid down or kept upside down after the blood sampling, it becomes possible to prevent leak of the blood, or when, after a portion of the specimen is taken with the stopper being detached, the stopper 10 is again attached, it becomes possible to prevent the stopper 10 from gradually rising up and consequently coming off, and thus, the container is kept free from problems that might impair functions as a sealed container.

In the sealed container 1 of one embodiment in accordance with the second aspect of the present invention, in the case when the entire leg portion B40 of the stopper 10 is in contact with the external wall surface 5 of the container 2, after repeatedly attaching and detaching the stopper 10 to and from the container, the blood inside the container sinks into a gap between the leg portion B40 and the external wall surface 5 of the container 2, and tends to contaminate the fingers of the operator. Therefore, the leg portion B40 preferably has an end portion which is formed along the external wall surface 5 of the container 2, without being in contact with the external wall surface 5 of the container 2.

In the sealed container 1 in accordance with the first aspect of the present invention, the materials constituting the container 2 and the stopper 10 are properly selected so as to satisfy the deflection temperature under load. In the second aspect of the present invention, the combination of materials constituting the container 2 and the stopper 10 is properly selected so that the deflection temperature under load of the container 2 and the stopper 10 satisfy the above-mentioned relationship.

The container 2 comprises a thermoplastic resin. The thermoplastic resin forming the container 2 is not particularly limited, and includes chain or cyclic olefin-based resins, styrene-based resins, acrylic-based resins, acrylonitrile-based resins, acrylonitrile-styrene-based resins, acrylonitrile-styrene-butadiene-based resins, ester-based resins, amide-based resins and modified cellulose-based resins.

The material used for forming the stopper 10 is not particularly limited, for example, in addition to the thermoplastic resins exemplified as the materials for the above-mentioned container, and includes thermoplastic resins, such as phenol-based resins, unsaturated ester-based resins, urea-based resins and melamine-based resins; metals such as aluminum and stainless; ceramics and the like.

The method of manufacturing the stopper 10 is not particularly limited, for example, and a cutting may be used, and a method in which the head portion 20 and the leg portion B40 are integrally molded by using an extrusion compression molding method, an injection molding method and the like and to this, inserting the leg portion A30 which is molded in a separated manner may also be used. Here, the head portion 20, the leg portion B40 and the leg portion A30 may of course be integrally molded.

The method of manufacturing the container 2 is not particularly limited, and a conventionally known injection molding method may be used.

By fitting the stopper 10 to the open portion of the container 2 thus formed, a sealed container 1 can be manufactured.

FIG. 4 is a semi-sectional view which shows a partially cutout portion of a sealed container 1a derived from the embodiment shown in FIG. 1. In the sealed container 1a, a stopper 10a is fitted to a container 2a. FIG. 5 is a semi-sectional view which shows a partially cutout portion of a stopper 10a, and FIG. 6 is a semi-sectional view which shows a partially cutout portion of a container 2a of FIG. 6.

In the sealed container 1a, the leg portion B40 which is extended downward from the head portion 20 of the stopper 10a, and is along the external wall surface 5 of the open end of the container 2a, and a portion 41 near the open end can be fitted to the external wall surface 5, since a ring-shaped rib 5a which protrudes outward is formed at the open end 3 of the container 2a. The other structures of the container and the stopper are the same as those of the embodiment shown in FIG. 1.

FIG. 7 is a semi-sectional view which shows a partially cutout portion of a sealed container 1b of another preferred embodiment of the sealed container of the present invention. In the sealed container 1b, the stopper 10b is fitted to the container 2. FIG. 8 is a semi-sectional view which shows a partially cutout portion of a stopper 10b.

In the sealed container 1b, a position of a fitting force exerted between the leg portion A30 of the stopper 10b and the internal wall surface 4 of the container 2 being greatest and a position of a fitting force exerted between the leg portion B40 of the stopper 10b and the external wall surface 5 of the container 2 being greatest are located at different positions in the longitudinal direction of the container 2. In other words, the internal diameter of the container 2 and the external diameter of the leg portion A30 are determined so that the greatest fitting force between the leg portion A30 which is extended downward from the head portion 20 of the stopper 10b and the internal wall surface 4 of the container 2 is exerted on an internal recessed side of the container 2 from the fitting portion 41 between the leg portion B40 and the external wall surface 5 of the container 2, that is, on the sealed end side, and a ring-shaped rib 31, which protrudes toward the internal wall surface 4 of the container 2, is formed on the leg portion A30. Such a ring-shaped rib 31 needs not to be formed on the leg portion A30 of the stopper 10b in a limited manner, and may be formed at the corresponding position of the internal wall surface 4 of the container 2 in a manner that it protrudes toward the leg portion A30. Moreover, the height and the number of the ring-shaped ribs 31 are not particularly limited, as long as no troubles are caused in forming the stopper through an injection molding method.

By forming the ring-shaped rib 31 in this manner, the container 2 is easily deformed into a shape with a narrowed opening, and therefore, even when the sealed container 1b is stored for a long period of time under high temperatures, it becomes possible to prevent leak of the blood after the sampling, and also to prevent the stopper 10 from rising up from the sealed container 1b to impair the functions as a sealed container.

The other structures of the container and the stopper are the same as those of the embodiment shown in FIG. 1.

FIG. 9 is a semi-sectional view which shows a partially cutout portion of a sealed container 1c of another preferred embodiment of the sealed container of the present invention. In the sealed container 1c, a stopper 10c is fitted to the container 2. FIG. 10 is a semi-sectional view which shows a partially cutout portion of the stopper 10c.

In the sealed container 1c, a surface layer 32, comprising a thermoplastic elastomer or a thermosetting elastomer, is formed at least at a portion of the leg portion A30, which is extended downward from the head portion 20 of the stopper 10c, contacting with the internal wall surface 4 of the container 2. By having such a surface layer 32 thereon, it becomes possible to further improve the sealing property.

The other structures of the container and the stopper are the same as those of the embodiment shown in FIG. 1.

The thermoplastic elastomer forming the surface layer 32 is not particularly limited, for example, and includes olefin-based, styrene-based, ester-based, amide-based and urethane-based ones. Each of these thermoplastic elastomers may be used alone, or two or more kinds of these may be used in combination. The thermosetting elastomer forming the surface layer 32 is not particularly limited, for example, and includes natural rubber-based, isoprene rubber-based, isobutylene-isoprene rubber-based, styrene-butadiene rubber-based, neoprene rubber-based and silicone rubber-based ones. Each of these thermosetting elastomers may be used alone, or two or more kinds of these may be used in combination.

Moreover, irrespective of the thermoplastic elastomer and the thermosetting elastomer, those which has a superior gas-barrier property with an oxygen permeation coefficient (25° C.) of preferably 10 times or less, more preferably 6 times or less, further preferably 3 times or less as much as that of isobutylene-isoprene-based cured rubber are preferable to improve airtightness as a sealed container.

The surface layer 32, which is preliminarily injection-molded or compression-cure-molded, may be fitted thereto, or the surface layer 32 may be integrally molded through an insert molding method.

A lubricant, such as various kinds of oils, waxes, fatty acid/fatty acid salts, fatty acid amides, surfactants, plasticizers, lubricating inorganic fine powder or lubricating organic fine powder, may be applied to the surface of the surface layer 32 so as to reduce frictional resistance in fitting the stopper 10c into the container 2. Moreover, these lubricants may be preliminarily blended in a thermoplastic elastomer or a thermosetting elastomer which forms the surface layer 32.

Moreover, an ethylene-vinyl acetate copolymer, an ethylene-acrylic acid copolymer, an ethylene-methacrylic acid copolymer, an ethylene-acrylic acid ester copolymer, an ethylene-methacrylic acid ester copolymer, polyethylene, polypropylene and the like having a high MFR value of preferably 30 or more, more preferably 50 or more, further preferably 70 or more, may be preliminarily blended in the thermoplastic elastomer or the thermosetting elastomer forming the surface layer 32 as a flowability improving agent in molding. In this case, the amount of blend of the flowability improving agent is preferably 20% by weight or less. When the amount of blend is more than 20% by weight, the elastic property as the elastomer tends to be adversely affected. The amount of blend is more preferably 10% by weight or less, further preferably to 5% by weight or less.

The surface layer 32 is preferably 80 or less in JIS A hardness or ASTM shore hardness A. When the hardness is more than 80, resistance exerted in fitting the stopper 10c into the container 2 tends to increase, and the adhesion to the inner face of the container 2 tends to be lowered, resulting in degradation in the operability and airtightness. More preferably, the hardness is 60 or less.

FIG. 11 is a semi-sectional view which shows a partially cutout portion of a sealed container 1d in accordance with another preferable embodiment of the sealed container of the present invention. In this sealed container 1d, a stopper 10d is fitted to the container 2. FIG. 12 is a semi-sectional view which shows a partially cutout portion of the stopper 10d.

In the sealed container 1d, a needle pipe insertable portion 60, comprising a thermoplastic elastomer or a thermosetting elastomer, is formed in the center of a partition wall portion 50 of the stopper 10d. By providing such a needle pipe insertable portion 60, the needle pipe is pierced into the sealed container without the necessity of removing the stopper 10d from the container 2 so that blood can be injected therein or the inside blood can be partially drawn therefrom.

The other structures of the container and the stopper are the same as those of the embodiment shown in FIG. 1.

With respect to the thermoplastic elastomer or the thermosetting elastomer forming the needle pipe inserting portion 60, the same elastomers as those described above may be used. Moreover, in incorporating this thermoplastic elastomer or thermosetting elastomer into the partition wall portion 50, a conventionally known method, such as fitting a preliminarily molded one thereto and integrally molding by using an insert-molding method, may be used.

The above-mentioned needle pipe inserting portion 60 is preferably 80 or less in JIS A hardness or ASTM shore hardness A. If the hardness is more than 80, the needle pipe piercing resistance tends to increase, and the needle hole sealing property tends to be lowered. The hardness is more preferably 60 or less.

FIG. 13 is a semi-sectional view which shows a partially cutout portion of a sealed container 1e in accordance with still another preferable embodiment of the sealed container of the present invention. In this sealed container 1e, a stopper 10e is fitted to the container 2. FIG. 14 is a semi-sectional view which shows a partially cutout portion of the stopper 10e.

In the sealed container 1e, an open portion 35 through which a needle pipe is inserted is formed in the center of the partition wall portion 51 of the stopper 10e, and the leg portion A30 which is extended downward from the head portion 20, and fitted to an internal wall surface of the container 2, comprises a thermoplastic elastomer or a thermosetting elastomer through which the needle pipe can be pierced. The open portion 35 through which the needle pipe is inserted needs not to be formed in the center, and the number of the open portions 35 is not limited to one, and a plurality of them may be formed.

With respect to the thermoplastic elastomer or the thermosetting elastomer, the same elastomers as those described above may be used. Moreover, the method of manufacturing the leg portion A30 is not particularly limited, and a leg portion A30 may be insert-molded onto a preliminarily molded stopper head portion 20, or a leg portion A30, separately molded, may be bonded thereto.

The other structures of the container and the stopper are the same as those of the embodiment shown in FIG. 1.

FIG. 15 is a semi-sectional view which shows a partially cutout portion of a sealed container 1f in accordance with another preferable embodiment of the sealed container of the present invention. In this sealed container 1f, a stopper 10f is fitted to the container 2. FIG. 16 is a semi-sectional view which shows a partially cutout portion of the stopper 10f.

In the sealed container 1f, an open portion 35 through which a needle pipe is inserted is formed in the center of the partition wall portion 51 of the stopper 10f, and the leg portion A30 which is extended downward from the head portion 20, and fitted to an internal wall surface of the container 2, comprises a thermoplastic elastomer or a thermosetting elastomer through which the needle pipe can be pierced, and an assistant leg portion 70, which reinforces the fitting force of the leg portion A30, and also reinforces the bonding strength or the fusing strength to the head portion 20, is also extended downward from the head portion 20.

The other structures of the container and the stopper are the same as those of the embodiment shown in FIG. 1.

FIG. 17 is a semi-sectional view which shows a partially cutout portion of a sealed container 1g in accordance with another preferable embodiment of the sealed container of the present invention. In this sealed container 1g, a stopper 10g is fitted to the container 2. FIG. 18 is a semi-sectional view which shows a partially cutout portion of the stopper 10g.

In the sealed container 1g, an open portion 35 through which a needle pipe is inserted is formed in the center of the partition wall portion 51 of the stopper 10g, and the leg portion A30 which is extended downward from the head portion 20, and fitted to an internal wall surface of the container 2, comprises a thermoplastic elastomer or a thermosetting elastomer through which the needle pipe can be pierced, and a leg portion B40, which is extended downward from the head portion 20, and further extended toward the bottom side of the container 2 beyond the fitting length of the leg portion A30, is formed, and the leg portion B40 has a portion which is in contact with the external wall surface 5 of the container 2 in the vicinity 41 of the open end of the container, and exerts a fitting force thereto, and a skirt portion 42 which is not in contact with the external wall surface 5, and does not exert the fitting force.

The skirt portion 42 has functions for blocking blood droplets which may be scattered in detaching the stopper after the blood-sampling, and for securing the safety of the operator.

The other structures of the container and the stopper are the same as those of the embodiment shown in FIG. 1.

With the above-mentioned structure, the sealed container of the present invention hardly causes slackening of the stopper even when used in combination with a container comprising a thermoplastic resin. The sealed container of the present invention, which is kept in a reduced atmospheric pressure state, is suitably used for a vacuum specimen-sampling container, such as a vacuum blood-sampling tube.

A vacuum specimen-sampling container which comprises the sealed container of the present invention, the inside being in a reduced atmospheric pressure state, also constitutes the present invention.

Effect of the Invention

The present invention is capable of providing a sealed container which comprises a container comprising a thermoplastic resin and a stopper which is hardly slackening even when used in combination with the container, and a vacuum specimen-sampling container comprising the sealed container.

BEST MODE FOR CARRYING OUT THE INVENTION

The present invention will be described in more detail by means of examples, however, the present invention is not intended to be limited by only these examples.

Examples 1, 2

A sealed container having the same structure as the sealed container 1g shown in FIG. 17 was manufactured.

(1) Manufacture of a Stopper

A stopper was manufactured by using materials shown in Table 1. Here, the structure and dimension of the stopper were shown in FIG. 19.

First, by using high-impact polystyrene ("PSJ polystyrene", deflection temperature under load (0.45 MPa): about 75° C., manufactured by PS Japan Corporation) and polypropylene ("SunAllomer", deflection temperature under load (0.45 MPa): about 95° C., manufactured by SunAllomer Ltd.), a head portion and a leg portion B were integrally molded through an injection molding.

Next, in accordance with combinations shown in Table 1, a styrene-based thermoplastic elastomer ("RABALON", JIS A hardness: about 50, manufactured by Mitsubishi Chemical Corporation) and an EPDM-based thermoplastic elastomer ("Santoprene", JIS A hardness: about 55, manufactured by AES Japan Ltd.) were inserted to predetermined positions of the resulting head portion and leg portion B, and a leg portion A was molded; thus, the stopper of FIG. 19 was manufactured.

(2) Manufacture of a Container and a Sealed Container

By using polyethylene terephthalate ("DIANITE", deflection temperature under load (0.45 MPa): about 69° C. manufactured by Mitsubishi Rayon Co., Ltd.), a container having 10.7 mm in internal diameter and 13.2 mm in external diameter of an open end portion, 100 mm in total length and 7 mL in capacity was injection-molded.

The stopper was pushed and inserted to the resulting container in a reduced atmospheric pressure state to obtain a sealed container of 6 mL (vacuum blood-sampling tube).

Comparative Examples 1 to 3

By using materials shown in Table 1, a stopper was manufactured by using the same method as Example 1. The structure and dimension of the stopper were shown in FIG. 20. Here, the stopper shown in FIG. 20 has a structure in which a portion 41 which exerts a fitting force onto an external wall surface of the container open end was removed from the stopper shown in FIG. 19.

A sealed container (vacuum blood-sampling tube) was obtained in the same manner as Example 1 except that the resulting stopper was used.

Comparative Example 4

A stopper was manufactured by using the same method as Example 1 except that materials shown in Table 1 were used, and a sealed container (vacuum blood-sampling tube) was obtained by using the same method as Example 1 except that the stopper was used.

TABLE 1

|  | Stopper | | | | | Container | |
| --- | --- | --- | --- | --- | --- | --- | --- |
|  | head portion and leg portion B | | | | | | |
|  | material | Deflection temperature underload (0.45 MPa)(° C.) | leg portion A material | structure | material | Deflection temperature underload (0.45 MPa)(° C.) | |
| Example 1 | high-impact polystyrene | 75 | styrene-based thermoplastic elastomer | FIG. 19 | polyethylene terephthalate | 69 | |
| Example 2 | polypropylene | 95 | EPDM-based thermoplastic elastomer | FIG. 19 | polyethylene terephthalate | 69 | |
| Comparative Example 1 | high-impact polystyrene | 75 | styrene-based thermoplastic elastomer | FIG. 20 | polyethylene terephthalate | 69 | |
| Comparative Example 2 | polypropylene | 95 | EPDM-based thermoplastic elastomer | FIG. 20 | polyethylene terephthalate | 69 | |
| Comparative Example 3 | low-density polyethylene | 45 | styrene-based thermoplastic elastomer | FIG. 20 | polyethylene terephthalate | 69 | |
| Comparative Example 4 | low-density polyethylene | 45 | EPDM-based thermoplastic elastomer | FIG. 19 | polyethylene terephthalate | 69 | |

Here, 0.5% by weight of an oleic acid amide-based lubricant was preliminarily blended in the respective thermoplastic elastomers.

High-impact polystyrene ("PSJ polystyrene", deflection temperature under load (0.45 MPa): about 75° C., manufactured by PS Japan Corporation)

Polypropylene ("SunAllomer", deflection temperature under load (0.45 MPa): about 95° C., manufactured by SunAllomer Ltd.)

Styrene-based thermoplastic elastomer ("RABALON", JIS A hardness: about 50, manufactured by Mitsubishi Chemical Corporation)

EPDM-based thermoplastic elastomer ("Santoprene", JIS A hardness: about 55, manufactured by Advanced Elastomer Systems Japan Ltd.)

Polyethylene terephthalate ("DIANITE", deflection temperature under load (0.45 MPa): about 69° C. manufactured by Mitsubishi Rayon Co., Ltd.)

(Evaluation)

With respect to the sealed containers manufactured in Examples 1 and 2 and Comparative Examples 1 to 4, water was vacuum-sampled immediately after the manufacturing, and drawing resistance was measured as an index of a fitting force of the stopper. Moreover, after the stopper had been opened and 1 mL of water had been partially drawn therefrom, the container was again sealed with the stopper and immediately subjected to the drawing resistance measuring. Thereafter, the container was again sealed with the stopper, and left at room temperature of about 25° C. for 10 minutes so that the stopper was observed as to whether or not it gradually rose.

Moreover, the same evaluations were carried out after the deformation under heat at 60° C. for one week since the formation.

Furthermore, by using an Instron-type material tester, a force required for drawing the stopper straight at a speed of 200 mm/min was measured, and it was defined as the drawing resistance.

The results are shown in Table 2.

respect to the sealed containers manufactured in Examples, no stopper rise was observed so that a superior sealing property was maintained.

Examples 3 to 7

Sealed containers having the same structure as the sealed container 1g shown in FIG. 17 were manufactured.

(1) Manufacture of a Stopper

A stopper was manufactured by using materials shown in Table 3 through a two-material injection-molding method. Here, the structure and dimension of the stopper were shown in FIG. 19.

Here, 0.5% by weight of an oleic acid amide-based lubricant was preliminarily blended in the respective thermoplastic elastomers.

(2) Manufacture of a Container and a Sealed Container

By using materials shown in Table 3, a container having 10.7 mm in internal diameter and 13.2 mm in external diameter of an open end portion, 100 mm in total length and 7 mL in capacity was injection-molded.

The stopper was pushed and inserted to the resulting container in a reduced atmospheric pressure state to obtain sealed container of 6 mL (vacuum blood-sampling tube).

Comparative Examples 5 to 9

(1) Manufacture of a Stopper

A stopper was manufactured by using materials shown in Table 3 through a two-material injection-molding method. Here, the structure and dimension of the stopper were shown in FIG. 20.

TABLE 2

|  | Immediately after manufacture | | | After deformation under heat at 60° C. for one week | | |
| --- | --- | --- | --- | --- | --- | --- |
|  | drawing resistance (kg) | re-drawing resistance (kg) | stopper rise | drawing resistance (kg) | re-drawing resistance (kg) | stopper rise |
| Example 1 | 4.4 | 2.0 | none | 4.5 | 1.8 | none |
| Example 2 | 4.1 | 1.8 | none | 4.4 | 1.7 | none |
| Comparative Example 1 | 3.2 | 1.1 | present | 3.6 | 0.6 | present |
| Comparative Example 2 | 3.5 | 1.1 | present | 3.5 | 0.4 | present |
| Comparative Example 3 | 3.4 | 1.0 | present | 3.6 | 0.6 | present |
| Comparative Example 4 | 3.9 | 1.7 | none | 3.6 | 0.5 | present |

Irrespective of the sealed containers manufactured in Examples and the sealed containers manufactured in Comparative Examples, the drawing resistance appeared to be in virtually the same level even after the deformation under heat after a lapse of time. However, this is because the thermoplastic elastomer of the leg portion adhered to the internal wall surface of the blood sampling tube made of polyethylene terephthalate after a lapse of time. In contrast, with respect to the re-drawing resistance, the sealed containers manufactured in Examples clearly had greater values in comparison with the sealed containers manufactured in Comparative Examples, resulting in a clear difference between these. As a result, with Here, 0.5% by weight of an oleic acid amide-based lubricant was preliminarily blended in the respective thermoplastic elastomers.

(2) Manufacture of a Container and a Sealed Container

By using materials shown in Table 3, a container having 10.7 mm in internal diameter and 13.2 mm in external diameter of an open end portion, 100 mm in total length and 7 mL in capacity was injection-molded.

The stopper was pushed and inserted to the resulting container in a reduced atmospheric pressure state to obtain a sealed container of 6 mL (vacuum blood-sampling tube).

TABLE 3

| | Stopper | | | | Container | |
|---|---|---|---|---|---|---|
| | head portion and leg portion B | | | | | |
| | material | Deflection temperature under load (0.45 MPa)(° C.) | leg portion A material | structure | material | Deflection temperature under load (0.45 MPa)(° C.) |
| Example 3 | ethylene propylene random copolymer | 70 | styrene-based thermoplastic elastomer | FIG. 19 | low-density polyethylene | 45 |
| Example 4 | high-impact polystyrene | 75 | styrene-based thermoplastic elastomer | FIG. 19 | low-density polyethylene | 45 |
| Example 5 | polypropylene | 95 | styrene-based thermoplastic elastomer | FIG. 19 | acrylonitrile copolymer | 74 |
| Example 6 | polypropylene | 95 | styrene-based thermoplastic elastomer | FIG. 19 | ethylene propylene random copolymer | 70 |
| Example 7 | polypropylene | 95 | styrene-based thermoplastic elastomer | FIG. 19 | polymethyl pentene | 80 |
| Comparative Example 5 | ethylene propylene random copolymer | 70 | styrene-based thermoplastic elastomer | FIG. 20 | low-density polyethylene | 45 |
| Comparative Example 6 | high-impact polystyrene | 75 | styrene-based thermoplastic elastomer | FIG. 20 | low-density polyethylene | 45 |
| Comparative Example 7 | polypropylene | 95 | styrene-based thermoplastic elastomer | FIG. 20 | acrylonitrile copolymer | 74 |
| Comparative Example 8 | polypropylene | 95 | styrene-based thermoplastic elastomer | FIG. 20 | ethylene propylene random copolymer | 70 |
| Comparative Example 9 | polypropylene | 95 | styrene-based thermoplastic elastomer | FIG. 20 | polymethyl pentene | 80 |

Ethylene propylene random copolymer ("SunAllomer", deflection temperature under load (0.45 MPa): about 70° C., manufactured by SunAllomer Ltd.)

High-impact polystyrene ("PSJ polystyrene", deflection temperature under load (0.45 MPa): about 75° C., manufactured by PS Japan Corporation)

Polypropylene ("SunAllomer", deflection temperature under load (0.45 MPa): about 95° C., manufactured by SunAllomer Ltd.)

Styrene-based thermoplastic elastomer ("RABALON", JIS A hardness: about 50, manufactured by Mitsubishi Chemical Corporation)

Low-density polyethylene ("NUC high-pressure-method polyethylene", deflection temperature under load (0.45 MPa): about 45° C., manufactured by Nippon Unicar Co., Ltd.)

Acrylonitrile ("Barex", deflection temperature under load (0.45 MPa): about 74° C., manufactured by Mitsui Chemicals, Inc.)

Polymethyl pentene ("TPX", deflection temperature under load (0.45 MPa): about 80° C., manufactured by Mitsui Chemicals, Inc.)

(Evaluation)

With respect to the sealed containers manufactured in Examples 3 to 7 and Comparative Examples 5 to 9, the drawing resistance was measured by using the same method as Example 1 immediately after the manufacture and after deformation under heat at 60° C. for one week.

The results are shown in Table 4.

TABLE 4

| | Drawing resistance (kg) | |
|---|---|---|
| | immediately after manufacture | after deformation under heat at 60° C. for one week |
| Example 3 | 3.6 | 2.1 |
| Example 4 | 3.7 | 2.2 |
| Example 5 | 3.6 | 1.6 |
| Example 6 | 3.6 | 1.7 |
| Example 7 | 3.5 | 1.7 |
| Comparative Example 5 | 3.1 | 0.4 |
| Comparative Example 6 | 3.1 | 0.4 |
| Comparative Example 7 | 3.3 | 0.5 |
| Comparative Example 8 | 3.2 | 0.5 |
| Comparative Example 9 | 3.3 | 0.5 |

Examples 8 and 9, and Comparative Example 10

Sealed containers having the same structure as the sealed container 1b shown in FIG. 7 were manufactured.

(1) Manufacture of a Stopper

A stopper was manufactured by using materials shown in Table 5 through a two-material injection-molding method. Here, the structure and dimension of the stopper were shown in FIG. 24.

Here, 0.5% by weight of an oleic acid amide-based lubricant was preliminarily blended in the respective thermoplastic elastomers.

(2) Manufacture of a Container and a Sealed Container

By using materials shown in Table 5, a container having 10.7 mm in internal diameter and 13.2 mm in external diameter of an open end portion, 100 mm in total length and 7 mL in capacity was injection-molded.

The stopper was pushed and inserted to the resulting container in a reduced atmospheric pressure state to obtain a sealed container of 6 mL (vacuum blood-sampling tube).

TABLE 5

| | Stopper | | | | Container | |
|---|---|---|---|---|---|---|
| | head portion and leg portion B | | | | | |
| | material | deflection temperature under load (0.45 MPa)(° C.) | leg portion A material | structure | material | deflection temperature under load (0.45 MPa)(° C.) |
| Example 8 | high-density polyethylene | 70 | high-density polyethylene | FIG. 24 | low-density polyethylene | 45 |
| Example 9 | polypropylene | 95 | polypropylene | FIG. 24 | polypropylene | 95 |
| Comparative Example 10 | low-density polyethylene | 45 | low-density polyethylene | FIG. 24 | low-density polyethylene | 45 |

High-density polyethylene ("NUC polyethylene", deflection temperature under load (0.45 MPa): about 70° C., manufactured by Nippon Unicar Co., Ltd.)

Low-density polyethylene ("NUC high-pressure-method polyethylene", deflection temperature under load (0.45 MPa): about 45° C., manufactured by Nippon Unicar Co., Ltd.)

Polypropylene ("SunAllomer", deflection temperature under load (0.45 MPa): about 95° C., manufactured by SunAllomer Ltd.)

(Evaluation)

With respect to the sealed containers manufactured in Examples 8 and 9 and Comparative Example 10, the drawing resistance was measured by using the same method as Example 1 immediately after the manufacture and after deformation under heat at 60° C. for one week.

The results are shown in Table 6.

TABLE 6

| | Drawing resistance (kg) | |
|---|---|---|
| | immediately after manufacture | after deformation under heat at 60° C. for one week |
| Example 8 | 2.2 | 1.7 |
| Example 9 | 3.6 | 1.5 |
| Comparative Example 10 | 1.8 | 0.3 |

With respect to the drawing resistance, the sealed containers manufactured in Examples had clearly high values in comparison with sealed containers manufactured in Comparative Example so that a superior fitting force was maintained.

INDUSTRIAL APPLICABILITY OF THE INVENTION

The present invention makes it possible to provide a sealed container which comprises a container comprising a thermoplastic resin and a stopper which is hardly slackening even when used in combination with the container, and a vacuum specimen-sampling container comprising the sealed container.

BRIEF DESCRIPTION OF THE DRAWINGS

[FIG. 1] a semi-sectional view which shows a partially cutout portion of one embodiment of a sealed container of the present invention

[FIG. 2] a semi-sectional view which shows a partially cutout portion of a stopper of the sealed container shown in FIG. 1

[FIG. 3] a semi-sectional view which shows a partially cutout portion of a container of the sealed container shown in FIG. 1

[FIG. 4] a semi-sectional view which shows a partially cutout portion of a sealed container 1a derived from the embodiment shown in FIG. 1

[FIG. 5] a semi-sectional view which shows a partially cutout portion of a stopper of the sealed container shown in FIG. 4

[FIG. 6] a semi-sectional view which shows a partially cutout portion of a container of the sealed container shown in FIG. 4

[FIG. 7] a semi-sectional view which shows a partially cutout portion of a preferred embodiment of a sealed container of the present invention

[FIG. 8] a semi-sectional view which shows a partially cutout portion of a stopper of the sealed container shown in FIG. 7

[FIG. 9] a semi-sectional view which shows a partially cutout portion of another preferred embodiment of a sealed container of the present invention

[FIG. 10] a semi-sectional view which shows a partially cutout portion of a stopper of the sealed container shown in FIG. 9

[FIG. 11] a semi-sectional view which shows a partially cutout portion of another preferred embodiment of a sealed container of the present invention

[FIG. 12] a semi-sectional view which shows a partially cutout portion of a stopper of the sealed container shown in FIG. 11

[FIG. 13] a semi-sectional view which shows a partially cutout portion of another preferred embodiment of a sealed container of the present invention

[FIG. 14] a semi-sectional view which shows a partially cutout portion of a stopper of the sealed container shown in FIG. 13

[FIG. 15] a semi-sectional view which shows a partially cutout portion of another preferred embodiment of a sealed container of the present invention

[FIG. 16] a semi-sectional view which shows a partially cutout portion of a stopper of the sealed container shown in FIG. 15

[FIG. 17] a semi-sectional view which shows a partially cutout portion of preferred embodiment of a sealed container of the present invention

[FIG. 18] a semi-sectional view which shows a partially cutout portion of a stopper of the sealed container shown in FIG. 17

[FIG. 19] a view which shows the structure and dimension of the stopper in Examples 1 and 2

[FIG. 20] a view which shows the structure and dimension of the stopper in Comparative Examples 1, 2 and 3

[FIGS. 21(a) to (c)] views which show a basic structure of a conventional vacuum blood-sampling system

[FIG. 22] a side view which shows a multiple blood-sampling needle

[FIG. 23] a perspective view which shows a state in which a blood-sampling is carried out by using a vacuum blood-sampling system

[FIG. 24] a view which shows the structure and dimension of a stopper formed in Examples 8 and 9, and Comparative Example 10

DESCRIPTION OF THE NUMERALS 1, 1a, 1b, 1c, 1d, 1e, 1f, 1g sealed container
2, 2a container
3 open end
4 internal wall surface
5 external wall surface
5a ring-shaped rib
10, 10a, 10b, 10c, 10d, 10e, 10f, 10g stopper
20 head portion
30 leg portion A
32 surface layer
35 vacuum blood-sampling needle
40 leg portion B
41 vicinity of open end
42 skirt portion
50, 51 partition wall portion
60 needle pipe insertable portion
70 assistant leg portion
80 vacuum blood-sampling container
81 stopper
82 blood-sampling tube
83 holder
84 blood-sampling needle holding hole
85 vacuum blood-sampling needle
86 hub
87, 88 needle tip
89 multiple blood-sampling needle
90 elastic sheath

The invention claimed is:
1. A sealed container, which comprises
a container with an end being closed and the other end being open, comprising a thermoplastic resin, and
a stopper being detachable and capable of sealing the open end of the container, the stopper having a head portion capable of being grasped, a leg portion A extending downward from the head portion, extending along an internal wall surface of the open end of the container, and being capable of exerting a fitting force to the internal wall surface, and a leg portion B being extending downward from the head portion, the leg portion B having an external contact surface extending downward from the head portion, and the external contact surface contacts throughout an external wall surface of the open end of the container, and the external contact surface being capable of exerting a fitting force to the external wall surface, and
the external contact surface having a deflection temperature, under a load of 0.45 MPa or 0.46 MPa, which is higher than a deflection temperature, under a load of 0.45 MPa or 0.46 MPa, of at least a portion of the container, which contacts the leg portion A of the stopper;
wherein the leg portion A of the stopper is made of a thermoplastic elastomer or a thermosetting elastomer or the leg portion A has a surface layer comprising thermoplastic elastomer or a thermosetting elastomer at least at a portion contacting the internal wall surface of the container; and,
wherein a position of the fitting force exerted between the leg portion A of the stopper and the internal wall surface of the container being greatest and a position of the fitting force exerted between the external contact surface of the leg portion B of the stopper and the external wall surface of the container being greatest are located at different positions in the longitudinal direction of the container.

2. A vacuum specimen-sampling container, comprising the sealed container according to claim 1, the inside thereof being in a reduced atmospheric pressure state.

3. The sealed container according to claim 1, wherein the deflection temperature, under a load of 0.45 MPa or 0.46 MPa, of the at least the portion of the leg portion B of the stopper, which contacts the container, is 60° C. or more, and the deflection temperature, under a load of 0.45 MPa or 0.46 MPa, of the at least the portion of the container, which contacts the leg portion A of the stopper, is 60° C. or more.

4. The sealed container according to claim 1, wherein the stopper has a needle pipe insertable portion comprising a thermoplastic elastomer or a thermosetting elastomer.

5. A vacuum specimen-sampling container, comprising the sealed container according to claim 4, the inside thereof being in a reduced atmospheric pressure state.

6. The sealed container according to claim 1, wherein a distance of the leg portion B of the stopper contacting with the external wll surface of the container is shorter than a distance of the leg portion A of the stopper contacting with the internal wall surface of the container in the longitudinal direction of the container.

7. The sealed container according to claim 6, wherein a position of the fitting force exerted between the leg portion A of the stopper and the internal wall surface of the container being greatest and a position of the fitting force exerted between the leg portion B of the stopper and the external wall surface of the container being greatest are located at different positions in the longitudinal direction of the container.

8. The sealed container according to claim 6, wherein the leg portion A of the stopper has a surface layer comprising a thermoplastic elastomer or a thermosetting elastomer at least at a portion contacting with the internal wall surface of the container.

9. The sealed container according to claim 6, wherein the stopper has a needle pipe insertable portion comprising a thermoplastic elastomer or a thermosetting elastomer.

10. A vacuum specimen-sampling container, comprising the sealed container according to claim 6, the inside thereof being in a reduced atmospheric pressure state.

11. The sealed container according to claim 1, wherein the leg portion A of the stopper has a surface layer comprising a thermoplastic elastomer or a thermosetting elastomer at least at a portion contacting with the internal wall surface of the container.

12. The sealed container according to claim 11, wherein the stopper has a needle pipe insertable portion comprising a thermoplastic elastomer or a thermosetting elastomer.

13. A vacuum specimen-sampling container, comprising the sealed container according to claim 11, the inside thereof being in a reduced atmospheric pressure state.

* * * * *